(12) United States Patent
He et al.

(10) Patent No.: US 7,129,266 B2
(45) Date of Patent: Oct. 31, 2006

(54) ANTIBIOTIC CYAN426-A

(75) Inventors: Haiyin He, Washington Township, NJ (US); Hui Yang, Monsey, NY (US); Ramunas Bigelis, Congers, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 486 days.

(21) Appl. No.: 10/735,953

(22) Filed: Dec. 15, 2003

(65) Prior Publication Data

US 2004/0127540 A1 Jul. 1, 2004

Related U.S. Application Data

(60) Provisional application No. 60/434,005, filed on Dec. 17, 2002.

(51) Int. Cl.
*A61K 31/4015* (2006.01)
*C07D 207/18* (2006.01)

(52) U.S. Cl. .................. 514/423; 548/530; 548/539; 514/424

(58) Field of Classification Search ............... 548/530, 548/539; 514/423, 424
See application file for complete search history.

(56) References Cited

FOREIGN PATENT DOCUMENTS

JP    2001247574 A2    9/2001

OTHER PUBLICATIONS

He et al (2002): Tetrahedron Letters, vol. 43 (9), pp. 1633-1636.*
West, R.R., et al., The Journal of Antibiotics, 49(10), pp. 967-973, (1996).
Chopra, I., et al., Antimicrob Agents Chemotherapy, 41, pp. 497-503, (1997).
Hiramatsu, K., et al., Curr. Opin. Infect. Dis., 11(6), pp. 653-658, (1998).
Breithaupt, Holger, Nat. Biotechnol, 17(12), pp. 1165-1169, (1999).
Ginzburg, E., et al., Int. J. Antimicrobial Agents, 16, pp. S39-S42, (2000).
Marchese, A., et al., Journal of Chemotherapy, 12-2, pp. 12-14, (2000).
Marchese, A., et al., Journal of Chemotherapy, 12-2, pp. 12-14, (2000) (English Abstract).
Suzuki, S., et al., The Journal of Natural Products, 63, pp. 768-772, (2000).
Koizumi, Fumito, et al., JP 2001247574 A2, Sep. 11, 2001 (English Abstract).

* cited by examiner

*Primary Examiner*—Golam M. M. Shameem
(74) *Attorney, Agent, or Firm*—Daniel B. Moran

(57) ABSTRACT

The invention relates to a new antibiotic designated Cyan426-A, to its production by fermentation, to methods for its recovery and concentration from the crude solutions, and to a process for its purification and to semisynthetic ethers of Cyan426-A, Cyan426-A-ethers.

10 Claims, 2 Drawing Sheets

ANTIBIOTIC CYAN426-A

"This application claims priority from copending provisional application, application No. 60/434,005 filed Dec. 17, 2002 the entire disclosure of which is hereby incorporated by reference."

FIELD OF THE INVENTION

The invention relates to a new antibiotic designated Cyan426-A, to its production by fermentation, to methods for its recovery and concentration from crude solutions, and to a process for its purification. The present invention includes within its scope the agent in dilute form, as a crude concentrate, and in pure form, and a filamentous fungus designated LL-Cyan426. The invention further relates to semisynthetic ethers of Cyan426-A, Cyan426-A-ethers.

BACKGROUND OF THE INVENTION

New improved antibiotics are continually in demand, for the treatment of diseases in man. According to the World Health Organization, more than 95% of the *Staphylococcus aureus* isolates worldwide are now resistant to penicillin and up to 60% are resistant to methicillin (Breithaupt, H. *Nat. Biotechnol.* 17(12), 1165–9 (1999). Resistance is spreading from hospital-acquired infections to community-acquired pathogens, such as pneumococci and tuberculosis. The structurally related glycopeptides, vancomycin and teicoplanin, are considered the ultimate antibiotics of choice for treatment of methicillin-resistant *S. aureus*, but alarmingly, the rate of vancomycin-resistant enterococci has been increasing each year (a. Ginzburg, E.; Namias, N.; Brown, M.; Ball, S.; Hameed, S. M.; Cohn, S. M. *Int. J. Antimicrob. Agents*, 16 (Suppl.), S39–S42 (2000); b. Chopra, I. J.; Hodgson, B. M.; Poste, G. *Antimicrob. Agents Chemother.*, 41, 497–503 (1997)) and there are cases of vancomycin-resistant *S. aureus* reported in industrial countries (a. Hiramatsu, K.; Hanaki, H.; *Curr. Opin. Infect Dis.*, 11(6), 653–8 (1998); b. Marchese A.; Schito G. C.; Debbia E. A. *Journal of Chemotherapy*, 12 Suppl 2, 12–4(2000)).

The medical community recognizes that there is an ongoing need for additional antibiotics. The search for new antibiotics which exhibit antibacterial activity against vancomycin-resistant isolates and having structures which are not derivatives of vancomycin are particularly appealing.

Cyan416-A and their ether derivatives are different from the known antibiotics currently used in clinical practice. Some related compounds described in the literature include: Suzuki, S., Hosoe, T., Nazawa, K., Kawai K., Yaguchi, T., Udagawa, S., Antifungal substances against pathogenic fungi, talaroconvolutins, from *Talaromyces convolutus*, The Journal of Natural Products, 2000, 63 (6), 768; West, R., Van Ness, J., Varming, A., Rassing, B., Biggs, S., Gasper, S., Mackernan, P. A., Piggot, J., ZG-1494a, a novel platelet-activating factor acetyltransferase inhibitor from *Penicillium rubrum*, The Journal of Antibiotics, 1996, 49 (10), 967. Reported in Japanese Patent Kokai Tokkyo Koho, 2001, JP 2001247574 A2 20010911, Koizumi, F., Hasegawa, K., Ando, K., Ogawa, T., Hara, A., is Antitumor GKK1032 manufacture with *Penicillium*.

However, all of the above disclosed compounds are distinct from the present invention.

BRIEF SUMMARY OF THE INVENTION

The invention relates to a new antibiotic Cyan426-A, to the production of this antibiotic by fermentation, to methods for the recovery and concentration of the antibiotic from crude solutions, and to processes for the purification of the antibiotic. The invention further includes a new microorganism useful in the preparation of the antibiotic compound Cyan426-A. Additionally, this invention relates to semisynthetic ethers of Cyan426-A, designated as Cyan426-A-ethers.

The invention includes within its scope the new antibiotics in diluted form, as crude concentrates and in pure form. The novel antibiotics are useful as antibacterial agents.

The new antibiotic designated Cyan426-A is formed during the cultivation under controlled conditions of a filamentous fungus.

The structure of the new antibiotic Cyan426-A is:

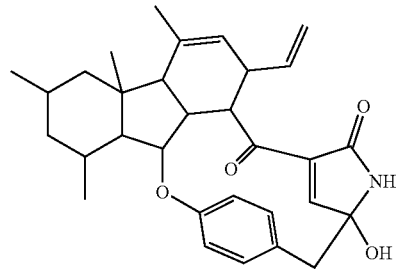

Figure 1:
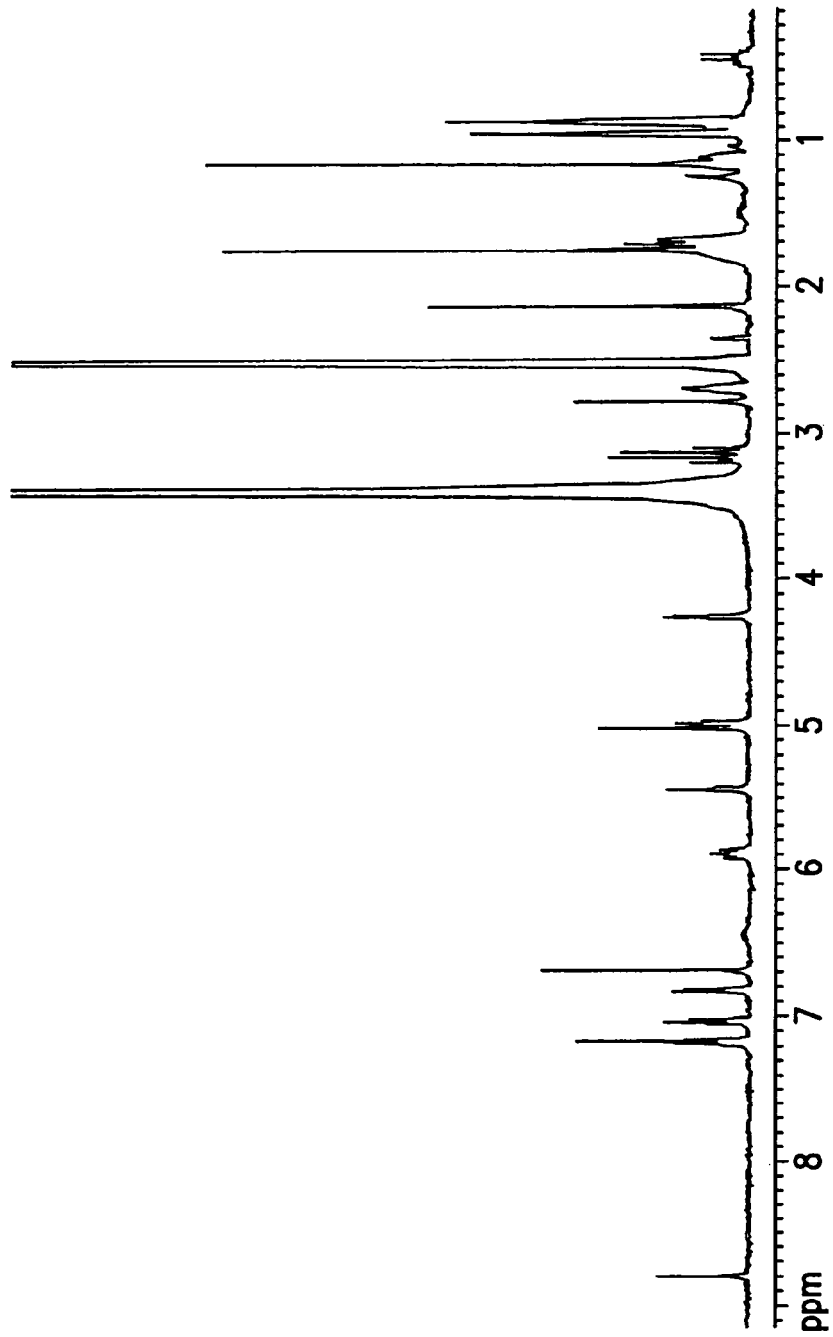
FIG. 1 Characteristic proton nuclear magnetic resonance (NMR) spectrum of compound designated Cyan426-A (400 MHz, DMSO-$d_6$).
Figure 2:
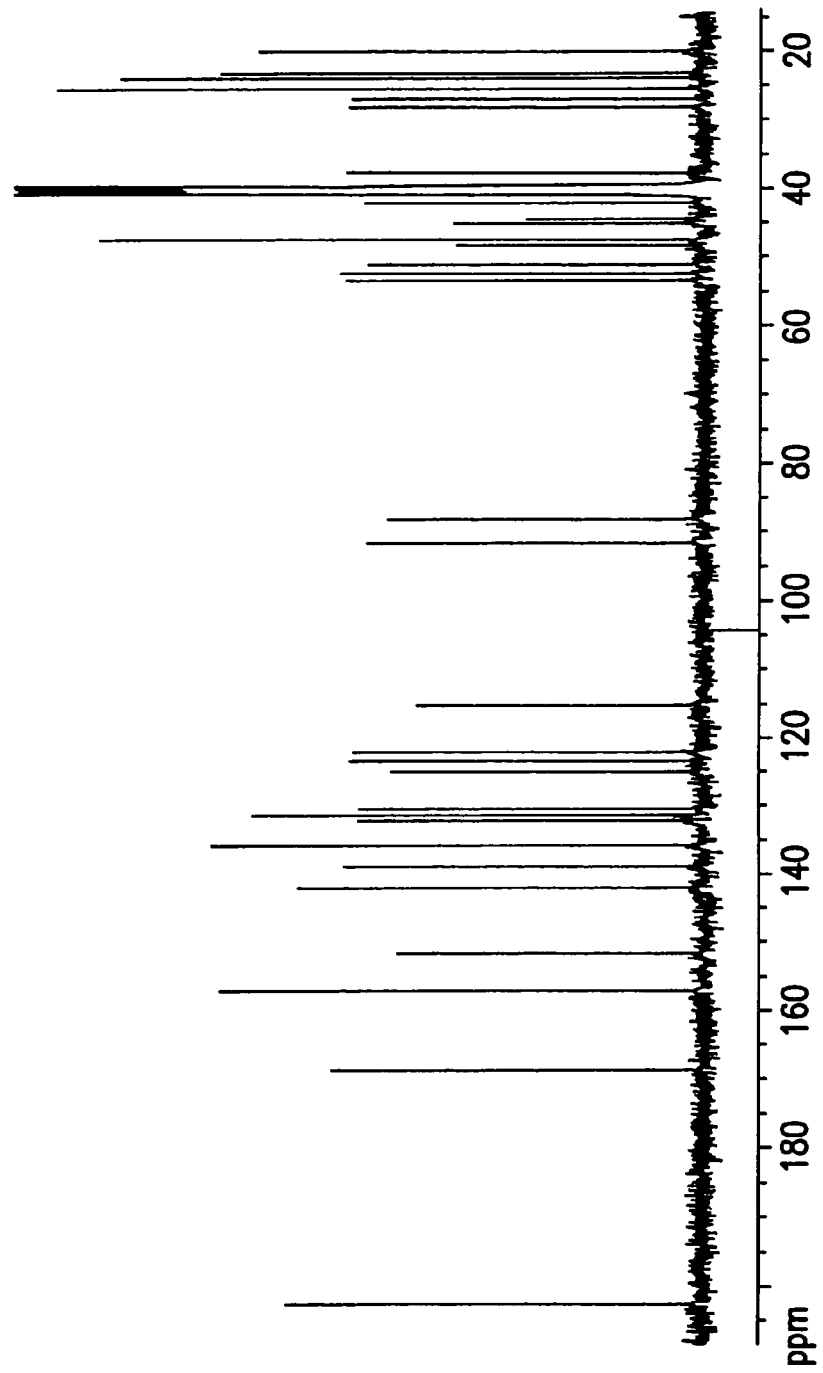
FIG. 2 Characteristic carbon-13 nuclear magnetic resonance spectrum (NMR) spectrum of compound designated Cyan426-A (100 MHz, DMSO-$d_6$).

The physico-chemical characteristics of Cyan426-A are as follows:

1. Molecular weight: 487 (ESIMS);
2. Apparent molecular formula: $C_{31}H_{37}NO_4$;
3. Proton nuclear magnetic resonance signals as shown in FIG. 1 (400 MHz, DMSO-$d_6$);
4. Carbon-13 nuclear magnetic resonance signals as shown in FIG. 2 (100 MHz, DMSO-$d_6$), with significant signals listed bellow:

| | | | | | |
|---|---|---|---|---|---|
| 202.4 | 168.2 | 156.6 | 151.3 | 141.6 | 138.5 |
| 135.4 | 131.6 | 130.9 | 130.0 | 124.4 | 122.7 |
| 121.4 | 114.7 | 91.0 | 87.6 | 52.8 | 51.7 |
| 50.4 | 47.8 | 46.9 | 44.3 | 43.8 | 41.4 |
| 37.2 | 27.7 | 26.6 | 25.0 | 23.5 | 22.8 |
| 19.7 | | | | | |

A further embodiment of the invention are compounds designated Cyan426-A-ether of the formula:

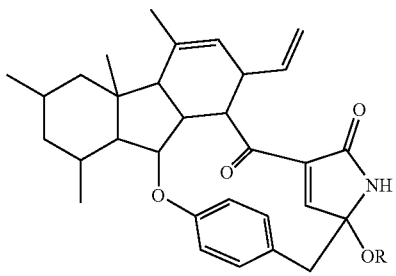

where R is lower alkyl of 1 to 6 carbon atoms.

The new antibacterial agent Cyan426-A is formed during the cultivation under controlled conditions of a filamentous fungus, LL-Cyan426.

This filamentous fungus is maintained in the culture collection of Wyeth Research, Pearl River, N.Y. 10965, as culture LL-Cyan426.

Description of Cyan 426

Culture LL-Cyan426 is that of a fungus, *Cylindrocarpon* sp., isolated from a sample collected from a mixed Douglas Fir hardwood forest located in Crane Island Preserve, Washington State, in 1993. The culture has been deposited with Agricultural Research Services Culture Collection (NRRL), National Center for Agricultural Utilization Research, Agricultural Research Service, U.S. Department of Agriculture at 1815 North University Street, Peoria, Ill. 61604 as NRRL30632.

The culture LL-Cyan426, identified as *Cylindrocarpon* sp., exhibits the following morphological features:

On oatmeal agar (Difco Laboratories), colony attaining a diameter of 82 mm after 3 weeks at 25° C. Colony mat Platinum Blonde (4B3) to Yellowish White (3A2) felted to floccose; reverse Cinnamon (6D6) to Sunburn (6D5); light brown pigment present and exudate absent.

On potato-dextrose agar (Difco) colony attaining a diameter of 75 mm in 3 weeks at 25° C. Colony mat Light Yellow (4A4) to Maize (4A6), felted to floccose; reverse center Venetian Red (8D8) to Persian Red (8E8), to margin Corn (4B5) to Mustard Brown (5B6); clear exudate accumulating near the center and pigment absent.

On Czapek-Dox agar (Difco) colony attaining a diameter of 80 mm in 3 weeks at 25° C. Colony mat Liver (8F6) to Raw Sienna (6D8), floccose to wooly; reverse center Dark Brown (7F8) to Rust Brown (6E8), to margin Grayish Orange (5B4); light brown pigment present and exudate absent.

On YM agar (Difco) colony attaining 81 mm in 3 weeks in 25° C. Colony mat center Pale Yellow (3A3) to Cream (4A3), felted to floccose, sulcate near center, reverse center Cognac (6E7) to Apricot (5B6); margin Champagne (4B4) entire pigment or exudate absent.

The characteristics of colony described were based on Methuen Handbook of colour (Kornerup, A. and Wanscher, J. H. $3^{rd\ ed.}$, 252p., Eyre Methuen, London, 1978.)

Conidiospores include micro-, and macroconidia. Microconidia hyaline, L-celled, obovoid to ellipsoid, 6–11×3–4 μm; macroconidia hyaline, 2-celled, cylindrical to fusoid with rounded ends and without Fusarium-type footcell, (16.5) 19–22×3–4 μm; chlamydospores light yellow to golden brown, globose to subglobose, 14–19 μm in diameter, terminal or in chain. Conidial mass in slimy heads, light cream color. Phialides with apical collar, simply, slender, sometimes wavy, 16–19×2 μm, or terminally on simple lateral branches or singly or in groups as termination of branches of penicillately branched conidiophores. Sterile stromatic structures bright orange.

For the production of this new antibacterial agent Cyan426-A the present invention is not limited to this particular organism. In fact, it is desired and intended to include the use of naturally-occurring mutants of this organism, as well as induced mutants produced from this organism by various mutagenic means known to those skilled in the art, such as exposure to nitrogen mustard, X-ray radiation, ultraviolet radiation, N'-methyl-N'-nitro-N-nitrosoguanidine, phages and the like. It is also desired and intended to include inter- and intraspecific genetic recombinants produced by genetic techniques know to those skilled in the art such as for example, conjugation, transduction and genetic engineering techniques.

It is a further object of the invention to provide a method of treating bacterial infections in mammals in need thereof with an effective amount of Cyan426-A or Cyan426-A-ethers.

It is an additional object of the invention to provide a pharmaceutical composition of Cyan426-A or Cyan426-A-ethers in the presence of one or more pharmaceutically acceptable carriers.

It is a further object of the invention to provide ethers of Cyan426-A, designated Cyan426-A-ethers prepared from Cyan426-A with acid and an alcohol.

Lower alkyl means a saturated aliphatic hydrocarbon radical of 1 to 6 carbon atoms. Examples of alkyl radicals include methyl, ethyl, propyl and the like.

Biological Activity

Standard Pharmacological Test Procedures

Methods for In Vitro Antibacterial Test Procedure

The minimum inhibitory concentration (MIC), the lowest concentration of the antibiotic which inhibits growth of the test organism, is determined by the broth dilution method using Muller-Hinton II agar (Baltimore Biological Laboratories) following the recommendations of the National Committee for Clinical Laboratory Standards [Methods for dilution antimicrobial susceptibility tests for bacteria that grow aerobically. Approved standard M7-A2. National Committee for Clinical Laboratory Standards, Villanova, Pa.].

An inoculum level of 5×105 CFU/ml, and a range of antibiotic concentrations (64–0.06 μg/ml) is used. The MIC is determined after the microtiter plates are incubated for 18 hours at 35° C. in an ambient air incubator. The test organisms comprise a spectrum of Gram-positive bacteria *Staphylococcus* sp., *Streptococcus pneumoniae*, *Enterococcus* sp., Gram-negative bacteria *Escherichia coli*, and the yeast *Candida albicans*. These organisms include recent clinical isolates that are resistant to piperacillin or vancomycin. MIC data of Cyan426-A are listed in Table 1.

TABLE 1

Antimicrobial activity of Cyan426-A.

| Test Organism | MIC (μg/ml) |
| --- | --- |
| *Staphylococcus aureus* GC 1131* | 2.0 |
| *Staphylococcus aureus* GC 4541* | 0.25 |
| *Staphylococcus aureus* GC 4543 | 1.0 |
| *Staphylococcus aureus* GC 2216 | 1.0 |

TABLE 1-continued

Antimicrobial activity of Cyan426-A.

| Test Organism | MIC (µg/ml) |
|---|---|
| *Staphylococcus haemolyticus* GC 4547* | 0.25 |
| *Enterococcus faecalis* GC 6189 | 0.50 |
| *Enterococcus faecalis* GC 4555 | 0.50 |
| *Enterococcus faecalis* GC 2242** | 0.50 |
| *Enterococcus faecium* GC 4556 | 1.0 |
| *Enterococcus faecium* GC 2243* | 1.0 |
| *Enterococcus faecium* GC 4558* | 0.50 |
| *Streptococcus pneumoniae* GC 1894 | 64 |
| *Streptococcus pneumoniae* GC 6242 | 16 |
| *Candida albicans* GC 3066 | 8.0 |
| *Escherichia coli* GC 4559 | 128 |
| *Escherichia coli* GC 4560 (imp) | 2.0 |

*Strains resistant to methicillin.
**Strain resistant to vancomycin.

The in vitro antimicrobial results show that the product according to the invention has significant activity against Gram-positive bacteria and yeast strains tested.

Antibiotic Cyan426-A derives its utility from its antibacterial activity. For example, this compound may be used in the suppression of bacterial infections, as a topical antibacterial agent or as a general disinfectant. This compound is not limited to the uses listed. In therapeutic use, the compound of this invention may be administered in the form of conventional pharmaceutical compositions appropriate for the intended use. Such compositions may be formulated as to be suitable for oral, parenteral or topical administration. The active ingredient may be combined in admixture with a nontoxic pharmaceutical carrier that may take a variety of forms depending on the form of preparation desired for administration, i.e. Oral, parenteral, or topical.

In therapeutic use, the compound of this invention may be administered in the form of conventional pharmaceutical composition appropriate for the intended use as an antibacterial. Such compositions may be formulated so as to be suitable for oral, parenteral or topical administration. The active ingredient may be combined in admixture with non-toxic pharmaceutical carrier may take a variety of forms, depending on the form of preparation desired for administration, i.e. oral, parenteral, or topical.

When the compound is employed as an antibacterial, it may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 0.01 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition of the host undergoing therapy.

Additionally, the antibacterially effective amount of the antibiotic of the invention may be administered at a dosage and frequency without inducing side effects commonly experienced with conventional antibiotic therapy which could include hypersensitivity, neuromuscular blockade, vertigo, photosensitivity, discoloration of teeth, hematologic changes, gastrointestinal disturbances, ototoxicity, and renal, hepatic, or cardiac impairment. Further the frequency and duration of dosage may be monitored to substantially limit harmful effects to normal tissues caused by administration at or above the antibacterially effective amount of the antibiotics of the invention.

The active compound may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA. The active compound may also be administered parenterally or intraperitoneally. Solutions or suspensions of the active compound as a free base or pharmacologically acceptable salt can be prepared in glycerol, liquid, polyethylene glycols and mixtures thereof in oils. Under ordinary conditions of storage and use, these preparations contain a preservative. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention accordingly provides a pharmaceutical composition which comprises a compound of this invention in combination or association with a pharmaceutically acceptable carrier. In particular, the present invention provides a pharmaceutical composition which comprises an antibacterially effective amount of a compound of this invention and a pharmaceutically acceptable carrier.

The present invention further provides a method of treating bacterial infections in warm-blooded animals including man, which comprises administering to the afflicted warm-blooded animals an antibacterially effective amount of a compound or a pharmaceutical composition of a compound of the invention. The invention will be more fully described in conjunction with the following specific examples, which are not to be construed as limiting the scope of the invention.

General Fermentation Conditions

Cultivation of LL-Cyan426 may be carried out in a wide variety of liquid culture media. Media which are useful for the production of Cyan426-A include an assimilable source of carbon, such as dextrin, sucrose, molasses, glycerol, etc.; an assimilable source of nitrogen, such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicon oil may be added as needed.

Culture LL-Cyan426 is inoculated on moist milk filter paper placed on the surface of a solid, agar medium containing malt extract, peptone, and yeast extract and incubated under stationary conditions at 22° C.

General Isolation Procedures of Cyan426-A:

The Cyan426-A is recovered from the fermentation broth by extracting cells with methanol. The methanol extract is evaporated under reduced pressure and the concentrate purified by HPLC on C18 columns using acidic acetonitrile in water to afford Cyan426-A.

As shown in Scheme I, Cyan426-A 1 is reacted with an alcohol ROH where R is lower alkyl of 1 to 6 carbon atoms in the presence of acid to afford ethers 2 designated Cyan426-A-ethers. In particular, reaction of Cyan426-A in an acidic methanol solution affords a methyl ether derivative (Cyan426-A-Me) where R is $CH_3$. Appropriate acids include but are not limited to hydrochloric, trifluoroacetic acid and sulfuric acid, preferably hydrogen chloride (HCl) in methanol in the presence of ether.

Scheme I

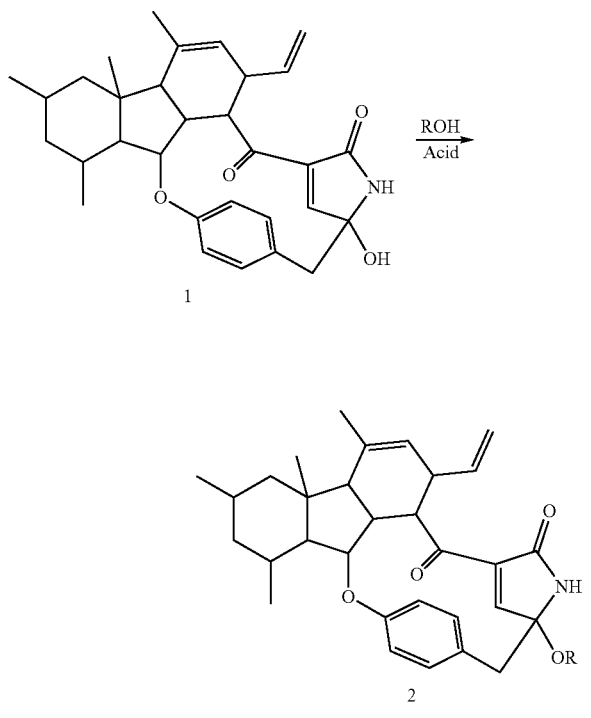

The invention is further described in conjunction with the following non-limited examples.

EXAMPLE 1

Inoculum Preparation

Fungal culture Cyan426 is plated on Bennett's agar medium (10 g/l Sigma D-glucose, 1 g/l Difco beef extract, 1 g/l Difco yeast extract, 2 g/l N-Z amine A, 20 g/l Difco agar) from a frozen 25% glycerol stock culture and incubated at 22° C. A small agar slice bearing mycelia is used to inoculate 50 ml of Difco potato-dextrose broth in a 250-ml Erlenmeyer flask. This liquid seed culture is shaken at 200 rpm at 22° C. for one week, and then used to inoculate production medium.

EXAMPLE 2

Fermentation

Production medium (1 L) consists of malt extract agar (25 g Difco malt extract, 5 g Difco peptone, 0.5 g Difco yeast extract, 20 g Difco agar) that is sterilized and poured into a 30×20×13 cm polypropylene tray covered with aluminum foil. The solidified agar is then overlaid with a sterile 28×46 cm sheet of nongauze milk filter paper cut from 18×22 in strips (KenAG Animal Care Group, Ashland, Ohio) that is sterilized separately. The production medium is inoculated by pipeting 50 ml of seed culture fluid onto the sheet of milk filter paper. The inoculated tray culture is incubated stationary at 22° C. After 2 weeks the milk filter paper bearing prolific mycelial growth is peeled from the surface of the agar, lyophilized for 5 days, and then extracted with 1.2 L methanol (pH 7).

EXAMPLE 3

Isolation and Purification of Cyan426-A

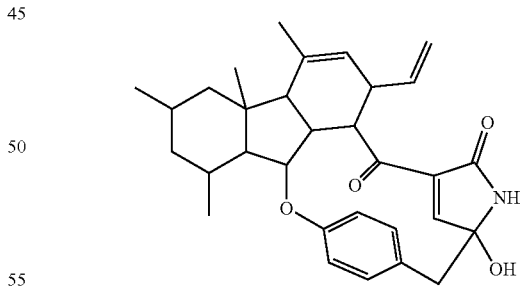

The methanol extract obtained in example 2 is separated by reverse phase HPLC on a C18 column (YMC ODS-A, 10 µm particle size, 70×500 mm), using a gradient of 90–100% acetonitrile in water containing 0.02% trifluoroacetic acid (TFA) over 40 min. The materials from a late fraction at 33 min, active in plate antibacterial assays, is further separated by a different HPLC system (YMC ODS-A, 5 µm, 10×250 mm column, 70–100% acetonitrile in water with 0.02% TFA over 25 min) to afford pure Cyan426-A (21.8 mg) as yellowish amorphous powder.

EXAMPLE 4

Methyl Ether Derivative (Cyan426-A-Me)

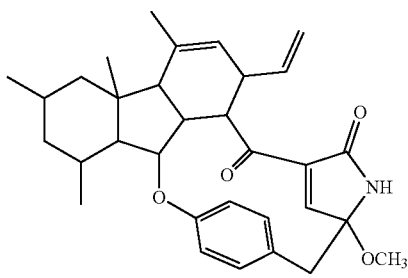

Cyan426-A (5.0 mg) is dissolved in a solution of 0.2 M HCl in 1:5 MeOH/Et$_2$O, and the resulting solution is stirred at ambient temperature for 24 hours. The reaction mixture is then chromatographed by HPLC on a C18 column (YMC ODS-A, 5 μm particle size, 30×250 mm) using a gradient solvent (70–100% acetonitrile in water containing 0.02% TFA) to afford a methyl ether derivative (Cyan426-A-Me, 2.2 mg). ESIMS (positive) m/z 502 (MH$^+$).

What is claimed is:

1. A compound having the formula

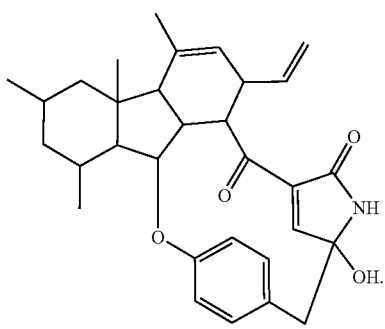

2. A method of treating a mammal affected by bacterial infections, which method comprises administering to said mammal an effective amount of the compound of claim 1.

3. A pharmaceutical composition comprising an effective amount of the compound of claim 1 together with a pharmaceutical acceptable carrier.

4. A compound having the formula:

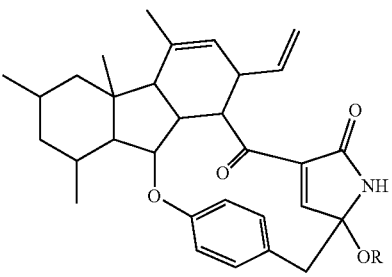

where R is lower alkyl of 1 to 6 carbon atoms.

5. A method of treating a mammal affected by bacterial infections, which method comprises administering to said mammal an effective amount of a compound of claim 4.

6. A pharmaceutical composition comprising an effective amount of a compound of claim 4 together with a pharmaceutical acceptable carrier.

7. The compound of claim 4, where R is methyl and having the formula

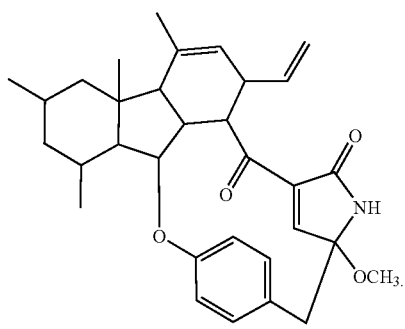

8. A process for the preparation of compounds of the formula:

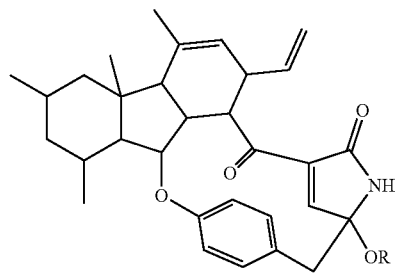

which comprises reacting a compound of the formula

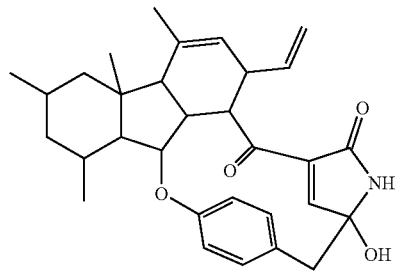

with an alcohol ROH where R is lower alkyl of 1 to 6 carbon atoms in the presence of an acid and isolating the compounds having the formula:
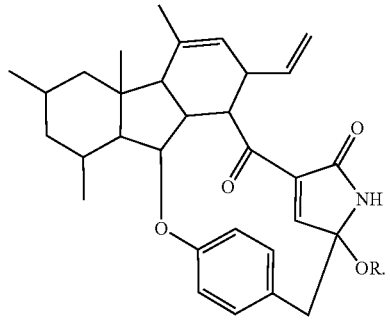
9. The compound according to claim 8 where R is CH$_3$ having the formula
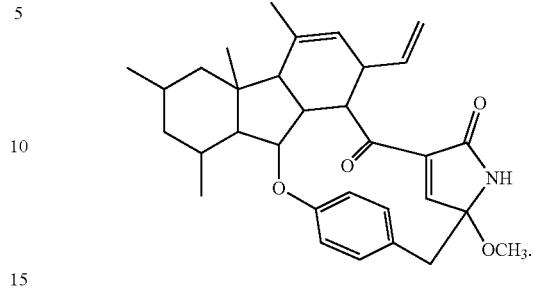
10. The acid according to claim 8 which is hydrogen chloride.
* * * * *